United States Patent [19]

Hamacher

[11] 4,246,894
[45] Jan. 27, 1981

[54] METHOD AND SYSTEM FOR ADMINISTERING A DISSOCIATIVE, UNCONSCIOUS TYPE OF ANESTHESIA

[76] Inventor: Edward N. Hamacher, Ste. 660, Southcenter Medical Bldg., West 105, 8th Ave., Spokane, Wash.

[21] Appl. No.: 42,027

[22] Filed: May 24, 1979

[51] Int. Cl.³ .................. A61B 19/00; B65D 83/04
[52] U.S. Cl. ................................. 128/1 R; 206/528
[58] Field of Search .................... 128/1 R, 214 C; 424/366, 244, 247, 267, 324; 206/528

[56] References Cited

PUBLICATIONS

"Physicians Desk Reference" *Medical Economics*, 25th Ed. pp. 1123, 1219.
"Merck Index" 9th Ed. pp. 310, 717.

*Primary Examiner*—Robert W. Michell
*Assistant Examiner*—Thomas Wallen
*Attorney, Agent, or Firm*—Seed, Berry, Vernon & Baynham

[57] ABSTRACT

A method and system of administering a dissociative unconscious type of anesthesia are disclosed. The method and system are designed for use in office surgical units and outpatient facilities. Administration by a nurse or a physician without anesthesia training can be done with minimum danger to the patient and minimum recovery time. The method and system utilizes the intravenous titration method of administration of a combination of drugs by which the patient is placed in a dissociative, unconscious state and maintained in this state until completion of the procedure, at which time the effect of the drugs is reversed by other drugs as desired. The intravenous anesthesia is supported by infiltration of a local anesthetic, such as Xylocaine. The combination of drugs include the basal hypnotic diazepam (Valium), a dissociated unconsciousness and general analgesia phencyclidine (Ketamine) and the narcotic analgesic Nisentil. The effects of the anesthetic can be reversed by the person administering the anesthesia as soon as their desired purpose has been accomplished.

7 Claims, No Drawings

METHOD AND SYSTEM FOR ADMINISTERING A DISSOCIATIVE, UNCONSCIOUS TYPE OF ANESTHESIA

BACKGROUND OF THE INVENTION

1. Field of the Invention

This invention relates to an anesthesia method and system for inducing a dissociative, unconscious state of anesthesia in patients.

2. Prior Art Relating to the Disclosure

Most surgical procedures today, including those carried out in office surgical units or outpatient facilities make use of the traditional anesthetics such as sodium pentathol and/or barbiturates. Many patients react adversely to the administration of sodium pentathol and during recovery become extremely nauseated. This not only causes distress to the patient but can create postoperative complications adversely affecting the patient. This is particularly true in plastic, reconstructive and cosmetic surgery where delicate portions of the facial muscles and bone structure are involved. Another problem with conventional anesthetic procedures in general use is that they must be administered by a trained anesthesiologist. This makes the medical procedure decidedly more expensive to the patient.

What has been needed, but not available, is an anesthesia system which is sufficiently safe that it can be administered in an office or outpatient clinic by a nurse or physician without anesthesia training. Also, what has been needed is an anesthetic system where the patient can be given commands and respond during the surgical procedure and where, once the patient recovers, only slight effects of nausea are encountered.

SUMMARY OF THE INVENTION

It is a primary object of this invention to provide a safe system of administering anesthesia for surgical procedures which is ideal for use in an office surgical unit or outpatient facility.

It is another object of this invention to provide an anesthesia system capable of being administered by a nurse, physician or other person without anesthesia training with minimum danger to the patient and minimum patient recovery time.

It is a further object of this invention to provide an anesthesia system administered by intravenous titration of a combination of drugs by which the patient is placed in a dissociative, unconscious state and maintained in that state until completion of the particular surgical procedure.

It is a further object of this invention to provide an anesthesia system wherein the effect of the drugs in the body is reversed or eliminated as soon as the desired surgical procedure is completed.

It is still a further object of this invention to provide an anesthesia system wherein, during the surgical procedure while the patient is under anesthesia, the patient can receive and respond to commands by the surgeon.

Lastly, it is one of the purposes of this invention to provide an anesthesia procedure wherein the time for recovery until the patient is able to be dressed and sent home is minimal, generally 15 to 45 minutes.

These and other objects are accomplished by administering a therapeutic dose of an anti-cholinergic agent such as atropine intravenously, then administering intravenously a sufficient amount of a basal hypnotic such as diazepam (Valium) intravenously at a dosage rate of up to 10 mg in 1 to 3 mg increments to relieve patient stress reaction, then administering intravenously by titration a dosage of 25 to 50 mg. of a phencyclidine derivative capable of inducing a state of dissociation and type of surgical anesthesia in the patient without rendering the patient unconscious at the rate of 1 to 3 mg. per minute, and lastly administering by intravenous injection 10 to 40 mg. of a narcotic analgesic, such as alphaprodine (Nisentil) at the rate of about 1 mg. per minute. The intravenous anesthesia is supported by infiltration of a local anesthetic, such as Xylocaine.

DETAILED DESCRIPTION OF THE INVENTION

The anesthesia system to be described has its greatest use for office surgical procedures and hospital outpatient facilities. It is particularly useful for plastic, reconstructive and cosmetic surgery, for minor and some major outpatient surgical procedures. The anesthesia system utilizes the intravenous titration method of administration of a combination of known drugs. The particular combination of drugs used to achieve the dissociative unconscious type of anesthesia includes a basal hypnotic such as diazepam (Valium), a dissociative unconsciousness and general analgesia phencyclidine such as Ketamine and a narcotic analgesic such as Nisentil.

All of the drugs used in the anesthesia system can be packaged separately in a compact unit with suitable instructions and used and administered by nurses, physicians or others without previous anesthesia training and with minimum danger to the patient. The anesthesia system is safe and is ideal for use without need for a trained anesthesiologist.

The procedure for administration of the various drugs is described below. It is generally advisable to give the patient orally a Combid (prochlorperazine maleate with isopropamide iodide) spansule 15 to 30 minutes prior to surgery to inhibit gastrointestinal spasms and motility, relieve anxiety and tension and control nausea and vomiting. The Combid spansule has a 12 hour release time when taken by mouth. It is also antiemetic, antispasmodic, antisecretory and reduces gastric secretions. The minimum-maximum dose is caps lq. 12 hours.

For most surgical procedures a barbiturate such as Seconal (secobarbital sodium capsules) may be given to the patient orally at the same time as the Combid. The dosage rate for Seconal may range from 1.5–3 gr. (100 mg.=1.5 gr.) For procedures lasting under one hour a dosage of 1.5 gr. is generally adequate.

The remaining drugs are administered intravenously, preferably using an intravenous solution of lactated Ringer's solution with 5% dextrose packaged in 500 cc plastic bags as a carrier. Immediately after the intravenous Ringer's solution is infused into the patient's vein, an anticholinergic agent such as atropine at a dosage rate of gr. 1/150 is immediately given. The atropine is used to reduce salivation, stabilize heart action, allow the patient to breathe easier and prevent laryngeal spasm. Thereafter, a sufficient amount of a basal hypnotic such as diazepam (Valium) is infused with the Ringer's solution in an amount generally up to 10 mg. in 1 to 3 mg. increments to relieve patient stress reaction and anxiety reaction to the phencyclidine derivative. The minimum and maximum effective dosages of Valium are, respectively, about 2.5 mg. and 20 mg. A phencyclidine derivative, such as Ketamine, is administered by intravenous titration with Ringer's solution at a rate of 1 to 3 mg. per minute up to a dosage of 25 to 50 mg. The maximum dosage should not exceed about 60 mg. to 70 mg. The dosage is usually not effective unless 15 or more mg. are administered. The phencyclidine derivative induces a state of dissociation in the patient and a type of surgical anesthesia without rendering the patient unconscious. It produces a peculiar state of unconsciousness in which the patient appears not to be asleep or anesthesized but rather disconnected from his surroundings. When entering this dissociative, cataleptic or unconscious state, the patient's eyes open widely and horizontal nystagmus occurs. When this occurs, the eyeballs become centered and appear to be in a fixed gaze. At this time the patient is considered to be pharmacologically isolated and now ready for injection by infiltration of a local anesthetic such as Xylocaine. By injecting the local anesthetic during the time that the Ketamine is at its maximum effect (as determined by the patient's eye signs-strabismus) the two drugs work as a team and enhance each other over a long period of time. Surgical procedures can continue for as long as 4.5 hours even though the Ketamine may have been completely detoxified by the patient's liver in as little as one hour. The preferred local anesthetic is Xylocaine administered 0.25% by local infiltration or specific block injections with Adrenaline 1:2,000,000 as a vasoconstrictor. Next an amount of a narcotic analgesic such as alphaprodine (Nisentil) is administered by intravenous titration at the rate of 1 mg. per minute up to an average dose ranging from 20 to 40 mg. The average dose is 20 mg.

During the surgical procedure, the amount of Ketamine, Valium and Nisentil administered by titration is adjusted to maintain the desired anesthetic level for the time period required for completion of the particular surgical procedure which can be as long as 4 to 5 hours.

At any time respiratory distress of the patient is noted, or after the surgical procedure is completed an antagonist for diazepam such as Antilirium is intravenously administered at a dosage of from 1 to 2 mg. Antilirium is an anti-cholinesterase agent which has the effect of reversing the effect of diazepam on the body. Antilirium may also be used after recovery of the patient to relieve confusion or excessive drowsiness.

During the surgical procedure, the drug promethazine (Phenergan) may be intravenously introduced along with the phencyclidine derivative mainly for potentiation, i.e. prolongation of the sedative effects of the phencyclidine derivative and narcotic analgesic Nisentil. Promethazine hydrochloride is effective if a need is shown by the patient for larger doses of the analgesic/tranquilizer combination, i.e. Nisentil-Valium combination. If greater than 1 hour of surgical time is necessary, 5 to 10 mg. of Nisentil has been found to give 1 to 2 hours of analgesia in conjunction with 2.5 to 5 mg. Valium for restlessness. The initial dose of Ketamine wears off in about 1 hour and cannot be prolonged without difficulty. In all cases Xylocaine, 0.25% with 1:2,000,000 Adrenaline injected into the skin and subcutaneous tissues in the area where the surgical procedure is to take place, gives excellent local anesthesia with good ischemia effect.

In cases where excitability of the patient is noted, Inapsine, ½ to 1 cc may be administered slowly intravenously with diazepam. Inapsine may, in some cases, be used in place of diazepam.

It has been found that administration of 5 to 10 mg. Nisentil will give 1 to 2 hours of analgesia in combination with 2.5 to 5 mg. Valium as needed for restlessness. If greater than 20 mg. Valium is used, the drug tends to lose effectiveness or cause excitability of the patient, in which case Inapsine may be substituted. The initial dose of Ketamine generally wears off in almost exactly 1 hour. Xylocaine administered by local infiltration in conjunction with Ketamine is usually adequate to reinforce the effect of the Ketamine.

After the surgical procedure is completed, the effect of Valium and Nisentil is reversed quickly by injection of Antilirium (1 to 10 mg. given slowly) and Narcan (0.2 to 0.6 mg.) preferably about 0.4 mg. The patient recovers quickly and is able to be dressed and sent home within 15 to 45 minutes. Retrograde amnesia is experienced by most patients for the entire procedure.

I claim:

1. A method of inducing a dissociative, unconscious type of anesthesia for surgical procedures which is safe and capable of being used in an office and being administered by a nurse or physician without anesthesia training, the process allowing a minimal recovery period for the patient, comprising:
    administering a therapeutic dose of an anti-cholinergic agent intravenously to stabilize heart action, reduce and prevent laryngeal spasm,
    administering intravenously a sufficient amount of the basal hypnotic diazepam (Valium) in 1 to 3 mg. increments up to 10 mg. to relieve patient stress reaction,
    administering intravenously by titration a dosage of from 25 to 50 mg. of a phencyclidine derivative at the rate of 1 to 3 mg. a minute to induce a state of dissociation in the patient without rendering the patient unconscious, and
    administering by intravenous titration 10 to 40 mg. of the analgesic alphaprodine at the rate of about 1 mg. per minute.

2. The method of claim 1 including potentiation of the sedative effects of the phencyclidine derivative by intravenous injection of 6 to 25 mg. promethazine hydrochloride (Phenergan).

3. The method of claim 1 including reversing the effect of the intravenous anesthesia after completion of the surgical procedure or as necessary for respiratory distress or to relieve confusion or excessive drowsiness by intravenous injection of from 1 to 2 mg. at a slow rate of Antilirium.

4. The method of claim 1 wherein a therapeutic amount of Seconal is administered orally to the patient with Combid prior to any infusion of the other drugs.

5. The method of claim 1 including supporting the intravenous anesthesia by infiltration of Xylocaine as soon as the phencyclidine takes effect in the patient.

6. The method of claim 1 wherein Inapsine is injected intravenously at a dosage of ½ to 1 cc as a substitute for Valium.

7. The method of claim 1 including the intravenous injection of 0.2 to 0.6 mg. Narcan during or after the surgical procedure.

* * * * *